United States Patent [19]
Rubin

[11] Patent Number: 5,466,258
[45] Date of Patent: Nov. 14, 1995

[54] ORBITAL IMPLANT

[75] Inventor: Peter A. D. Rubin, Boston, Mass.

[73] Assignee: Porex Surgical, Inc., College Park, Ga.

[21] Appl. No.: 151,373

[22] Filed: Nov. 12, 1993

[51] Int. Cl.⁶ .................................................... A61F 2/14
[52] U.S. Cl. ................................................. 623/4; 623/5
[58] Field of Search .......................... 623/4, 5, 11, 16

[56] References Cited

U.S. PATENT DOCUMENTS

| | | | |
|---|---|---|---|
| 2,467,401 | 4/1949 | Murphey et al. | 623/4 |
| 2,661,480 | 12/1953 | Rosen et al. | 623/4 |
| 4,731,077 | 3/1988 | Allen. | |
| 4,976,731 | 12/1990 | Perry. | |
| 5,300,115 | 4/1994 | Py | 623/4 |

FOREIGN PATENT DOCUMENTS 456249  4/1949  Canada ..................................... 623/4

*Primary Examiner*—David Isabella
*Assistant Examiner*—Laura Fossum
*Attorney, Agent, or Firm*—Lane, Aitken & McCann

[57] ABSTRACT

An orbital enucleation implant is made out of porous material, such as porous polyethylene. The implant is shaped to have a conical posterior projection to provide for additional volume augmentation and a superior projection to fill out and prevent any superior sulcus deformity. A cavity or holes are provided in the superior projection to provide a site for attachment of the superior rectus muscle. A flange or lip is provided extending between the lateral sides of the implant around the inferior surface of the implant to provide a site for attachment of extraocular muscles.

21 Claims, 2 Drawing Sheets

ORBITAL IMPLANT

This invention relates to an orbital enucleation implant and, more particularly, to an orbital enucleation implant shaped to reduce deformation of the eye socket attributed to enophthalmos.

When an eye is removed typically because of trauma, tumor, pain or cosmesis, the eye is replaced with an orbital implant. The orbital implant serves to replace the volume lost as a result of the enucleation and preferably enhances the motility of the eye socket. As a result of the enhanced movement of the eye socket, improved movement is achieved of the overlying ocular prosthesis, which is designed to simulate the appearance of a natural eye. An ideal orbital implant will have good soft tissue coverage, not migrate, be biocompatible, have minimal risk for infection and ultimately enhance the motility of the ocular prosthesis.

Over the past several decades, numerous orbital implants have been introduced in an effort to improve the motility of ocular prostheses. Most of these designs have been spherical in shape or slight modifications of the spherical shape. Modifications were typically designed to facilitate attachment of the extraocular muscles to the orbital implant or to provide a coupling between the orbital implant and an overlying ocular prostheses. Significant problems have arisen with many of the older implants because of increased risk of infection, migration and even extrusion of the orbital implants from the eye socket.

In those cases in which the implant is well tolerated within the orbit, the eyelid and orbit take on an unnatural sunken appearance independent of the ocular prosthesis. This condition is attributable to a shrinking or sinking back of the soft tissues of the eye socket and is referred to as enophthalmos. There are several mechanisms which account for enophthalmos in an anophthalmic socket, which is an eye socket without a natural eye, including: (1) lost orbital volume attributed to the absence of an eye (typically, an orbital implant is less than 20 millimeters in diameter whereas the eyeball is typically 24 millimeters in diameter in an average eye); (2) atrophy of the surrounding orbital soft tissue (fat and muscle); (3) lack of support of fatty tissue (pre-aponeurotic fat pad) that lies in front of the levator muscle; and (4) torsion (posterior rotation) of the levator, superior rectus muscle complex. Clinically, enophthalmos is manifested by a finding of a deep superior sulcus in the form of a hollowing out of the upper eyelid. The mechanisms (3) and (4) listed above contribute most directly to hollowing of the superior sulcus. By increasing the size of the ocular prosthesis, the unnatural appearance caused by lost orbital volume can be mitigated. However, the increased size of the prosthesis adds bulk to the prothesis and limits its motility and provides additional weight bearing strain on the lower eyelid.

SUMMARY OF THE INVENTION

The present invention is designed to overcome the above-described problems with the prior orbital implants and makes use of several unique features.

In accordance with the invention, the material of the implant is an open-celled porous material such as porous polyethylene or hydroxyapatite. Porous polyethylene, marketed by the assignee of this application and sold under the trademark MEDPOR has been successfully used as implants throughout the body. The porous polyethylene material is biocompatible and permits fibrovascular ingrowth into the implant decreasing its chance for migration or extrusion.

The implant of the invention comprises a generally oblong body portion defining a posterior conical projection, which provides added volume replacement for the lost volume resulting from enucleation. A superior projection helps fill out the superior sulcus deformity commonly seen in anophthalmic sockets, supports the levator muscle and pre-aponeurotic fat pad and inhibits torsion of the levator muscle complex. A flange extends between the lateral sides of the implant around the inferior surface of the implant adjacent to the anterior of surface of the implant and provides a site for the attachment of the extraocular muscles which can be sutured to the implant.

DESCRIPTION OF THE PREFERRED EMBODIMENTS

Figure 1:
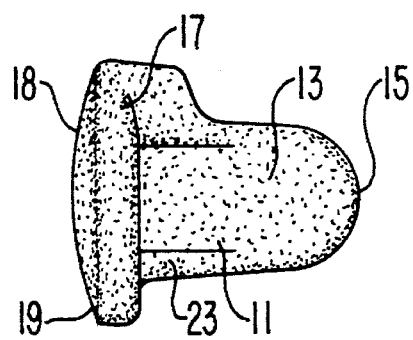
FIG. 1 is a side view in elevation of the orbital implant of the invention.
Figure 2:
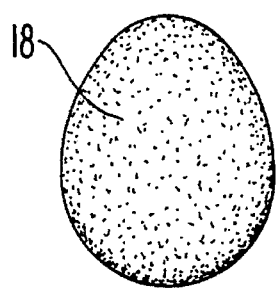
FIG. 2 is a front view in elevation of the implant of the invention showing the anterior surface of the implant.
Figure 3:
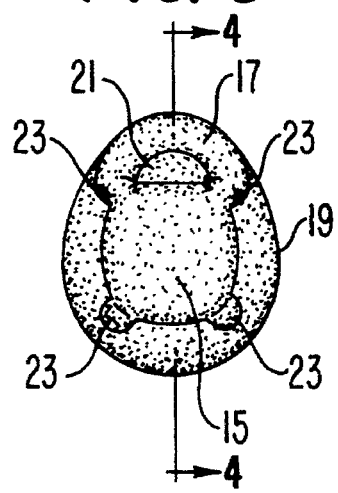
FIG. 3 is a rear view in elevation of the orbital implant of the invention.
Figure 4:
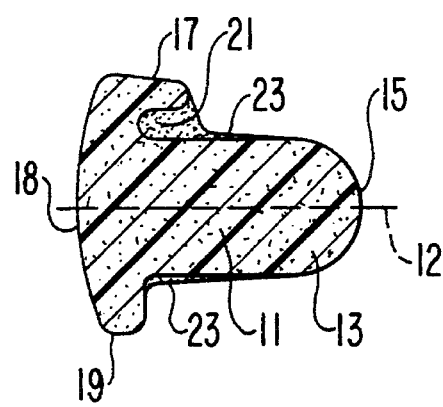
FIG. 4 is a sectional view of the implant taken along the line 4—4 of FIG. 3.
Figure 5:
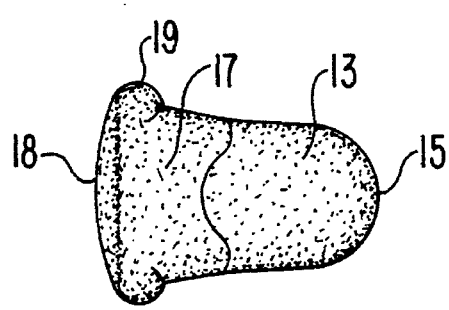
FIG. 5 is a top plan view of the orbital implant of the invention.

The implant of the invention shown in FIGS. 1–6 comprises a generally oblong body 11 elongated along an axis 12 extending in the anterior to posterior direction. The oblong body defines a generally conical posterior projection 13 extending along axis 12 and terminating in a dome-shaped posterior surface 15. The conical projection 13 is shaped to parallel the orbital contours of the eye socket and has a dimension along the axis 12 so that it will extend back into the orbit through the opening for the optic nerve in Tenon's capsule. A superior projection 17 is provided near the anterior side of the implant projecting along a vertical axis at about 90 degrees to the axis 12 of the posterior projection 13. The superior projection 17 helps fill out any superior sulcus and prevents posterior migration of the preaponeurotic fat pad. In addition, the superior projection 17 serves to support the levator muscle and prevent torquing of the levator superior rectus muscle complex. In this manner, the superior projection 17 prevents that aspect of enophthalmos manifested as a hollowing out of the upper eyelid. The superior projection 17 is provided with an oblong cavity 21 extending forwardly from the posterior surface of the projection 17. The cavity 21 serves to receive the superior rectus muscle which is sutured to the implant in this cavity.

The anterior surface 18 of the implant is curved in two dimensions with a greater curvature in the horizontal direction than in the vertical direction. The inferior side of the curved anterior surface terminates in a flange 19 which has a rounded edge and which extends between the lateral sides of the implant around the inferior surface of the implant. The curved anterior surface of the implant extends between the top surface of the superior projection 17 and the edge of the flange 19. The flange 19 provides a site for suturing the lateral, medial, and inferior rectus muscles to the implant. Because of the characteristics of the porous material, a conventional surgical needle can be easily passed through the flange 19 and the anterior wall of the cavity 21 to suture the muscles to the implant at these sites. If desired, holes may be provided in the flange 19 and in the anterior wall of the cavity 21 to receive the sutures. The hooded structure defining the cavity 21 is provided to ensure that the projection 17 is of sufficient strength while reducing the weight of the structure and, at the same time, providing a convenient site to attach the superior rectus muscle to the anterior side of the implant. The conical projection 13 is flattened on the superior side extending to the cavity 21 to provide a platform to receive the superior rectus muscle. Similarly, the inferior side and each of the two lateral sides are flattened extending to the flange 19 to provide a platform to position each of the inferior, lateral and medial rectus muscles and to define convenient sites for suturing these muscles to the flange 19. The flattened surfaces define flutes 23 extending from the corners joining the flattened surfaces of the conical posterior projection to the flange 19 or the junction of the flange 19 with the superior projection 17 to define channels in which the rectus muscles are positioned.

The surface of porous implant materials, such as the Porex MEDPOR material or the hydroxyapatite is typically rough. The anterior surface of the implant comes into contact with overlying Tenoh's tissue and conjunctiva and this rough surface could cause or contribute to erosion of this thin overlying tissue. To prevent such erosion, the anterior surface of the implant around the ocular prostheses is covered with fascia or sclera. Alternatively, or in addition, the anterior surface may be made smoother providing smaller pore sizes on the anterior surface than in the remainder of the implant. As a further alternative, the anterior surface may be coated with gelatin or polyglactin to smooth out the surface. Polyglactin will tend to resorb leaving a fibrous pseudocapsule on the surface to provide a smoother interface between the implant and the overlying tissue thus reducing the chances of the surface of the implant inducing erosion of the overlying tissue.

In the procedure to insert the implant in an anophthalmic socket, the implant is first soaked in antibiotic solution and then the anterior surface of the implant is covered with tissue, such as fascia or sclera. The tissue is secured to the anterior surface of the implant by sutures tying the tissue to the flange 19 between the sites at which the extraocular muscles will be attached to the implant. The implant is then placed within the Tenon's capsule with the posterior projection 13 being pushed through the optic nerve opening in the posterior side of the Tenon's capsule. The optic nerve opening will be widened to accommodate the projection 13 by the action of pushing the projection 13 through the opening. The implant is oriented to aim the superior projection 17 superiorly so that it will support the levator muscle in the top of the orbit. The superior rectus muscle is inserted into the cavity 21 and sutured in place by sutures passing through the wall between the inner end of this cavity and the anterior surface. The lateral, medial, and inferior rectus muscles are positioned to lie along the flat surfaces on the lateral and inferior sides of the implant between the flutes 23 and are sutured to the implant by sutures passing through the flange 19. The anterior Tenon's tissue is then closed around the anterior surface of the implant over fascia and secured with sutures. Then the conjuctiva is closed over the anterior surface with sutures. A conformer is then placed over the closed conjuctiva. After a period of 6–8 weeks to allow for the tissue to heal, the conformer is removed and an ocular prosthesis is fitted in place over the tissue covering the anterior surface.

Figure 6:
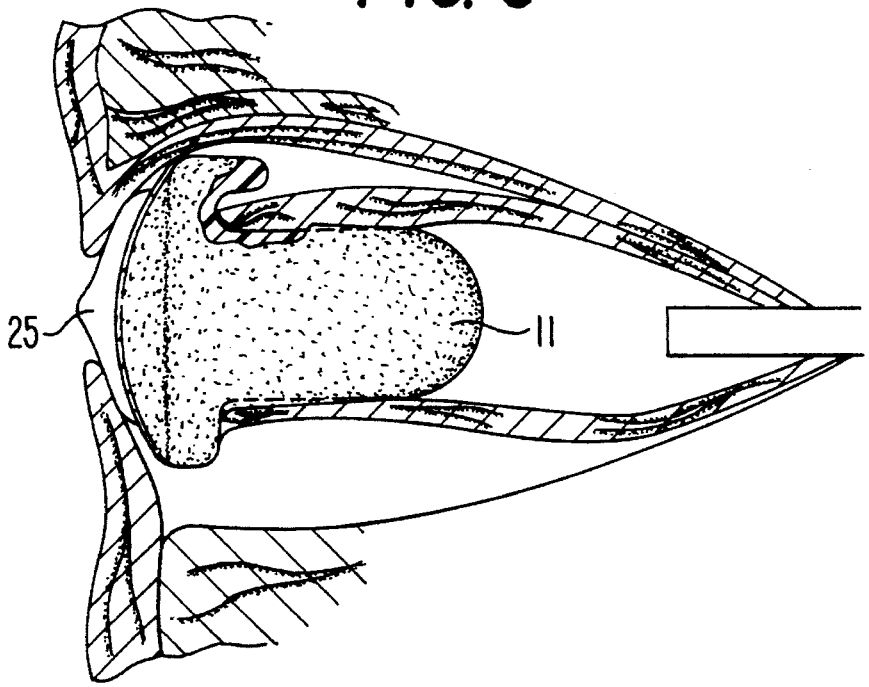
FIG. 6 is a sectional view showing the implant in place in an eye socket coupled to an ocular prosthesis.
Figure 7:
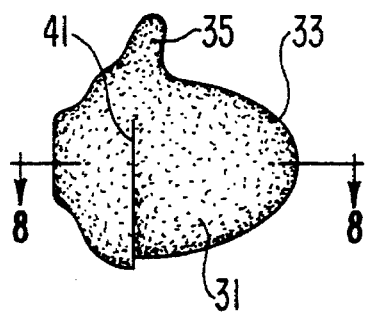
FIG. 7 is a side view in elevation of an alternative embodiment of the implant of the invention.
Figure 8:
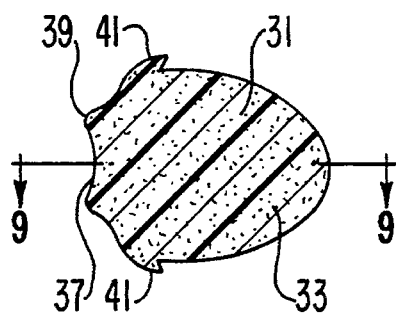
FIG. 8 is a horizontal sectional view taken along line 8—8 of FIG. 7.
Figure 9:
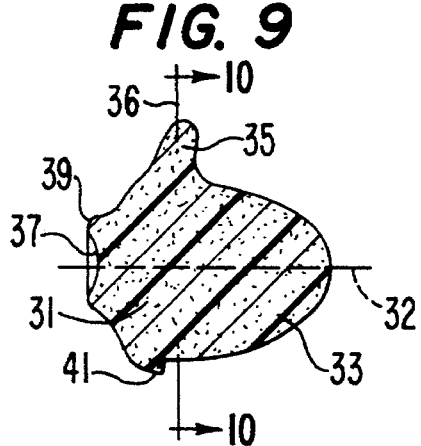
FIG. 9 is a vertical sectional view of the implant taken along the line 9—9 of FIG. 8.
Figure 10:
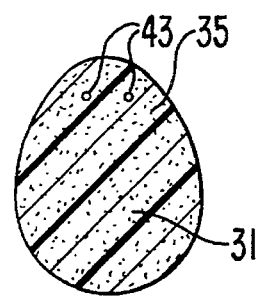
FIG. 10 is a vertical sectional view taken along the line 10—10 of FIG. 9.

FIG. 6 illustrates the results of a completed procedure with the implant and an ocular prosthesis 25 in place coupled to the anterior face of the implant through the tissue sandwiched between the implant and the ocular prosthesis. The dimension of the implant and prosthesis combination along the anterior to posterior axis 12 is greater than the diameter of the eye which it replaces by about 10 to 15%. The dimension of the implant itself along the axis 12 is a little less than the diameter of the eye being replaced. A typical eyeball has a diameter of about 24 millimeters and the dimension of the implant along the anterior to posterior axis to replace the typical eye is 21 to 22 millimeters. For a typical eyeball having a 24 millimeter diameter, the dimension of the superior projection 17 measured from the axis 12 is about 11 millimeters.

The alternative embodiment of the implant shown in FIGS. 7–10 may be described as comprising a generally spherical core 31 on which is formed a generally conical posterior projection 33 which extends along an anterior to posterior axis 32. A superior projection 35 having a rounded superior surface is also formed on the generally spherical core 31. The superior projection 35 is thinner in the anterior to posterior direction than it is laterally to provide a flattened configuration approximating that of a flattened paraboloid. The projection 35 extends along the vertical axis of the spherical core 31 at approximately 90 degrees to the axis 32 of the posterior projection 33. The anterior surface of the implant is formed with a central depression 37 surrounded by a circular peripheral ridge 39. Forward of the central vertical lateral plane of the spherical core and also anterior to the superior projection 35 is a lip 41 which extends between lateral sides of the core 31 around the inferior side of the core.

The conical projection 33 parallels the normal orbital contours of the eye socket and this projection and the superior projection 35 perform the same functions as the corresponding projections in the embodiment shown in FIGS. 1–6. The lip 41 provides a site for suturing the extraocular muscles to the implant. Two holes 43 are provided at the base of the superior projection 35 extending through this projection. Sutures attached to the superior rectus muscle are passed through these holes and are tied down in a stable fixed position to attach the superior rectus muscle to the implant. Holes may also be provided in the lip 41 to receive the sutures for the extraocular muscles.

The contour of the anterior surface of the implant comprising the depression 37 and the ridge 39 serve to increase coupling of the overlying ocular prosthesis to the implant. The depression 37 in the center of the anterior surface is to permit the central portion of the ocular prosthesis to have sufficient depth to provide good simulation of the depth of the iris of the eye being simulated. The ridge permits greater coupling strength between the implant and the ocular prosthesis. Around the ridge 39, the anterior surface of the implant is flattened compared to the imaginary spherical surface of the core 31. These flattened surface areas permit easier coverage of the implant by the conjunctiva and Tenon's tissue and permits more of the volume augmentation of the implant to be present deeper in the orbit or eye socket.

As described above, the preferred embodiments of the invention employ both a posterior projection of a size to extend through the optic nerve opening of the Tenon's capsule and a superior projection. Each of the projections, as described above performs different functions and an implant could be used without the superior projection or, alternatively, without the posterior projection and the corresponding advantages and functions of the employed feature would still be obtained.

The implants illustrated in the drawings are symmetrical about the vertical central plane bisecting the implant. This feature enables the implant to be used either in the left or right orbit. If this feature of symmetry is not employed, slots may be provided on the posterior projection of the implant to define sites for attachment of the oblique extraocular muscles. In addition, the lateral portion of the implant could be truncated for the purposes of deepening the lateral sulcus.

As described above, the implant is preferably made out of a porous polyethylene or, alternatively, out of hydroxyapatite. Other materials, including non-porous material, may be used for the implants, such as acrylic.

These and other modifications may be made to the above-described specific embodiments of the invention without departing from the spirit and scope of the invention, which is defined in the appended claims.

I claim:

1. An orbital enucleation implant for replacing a volume of an eyeball in an anophthalmic eye socket of an eye comprising a body of biocompatible material, said body being shaped to have a generally elongated body defining a posterior conical projection extending along an axis and shaped to parallel bony orbital contours of a posterior portion of the eye socket and, an anterior surface shaped, sized and positioned to be coupled to an ocular prosthesis which will extend under and be overlapped by upper and lower eyelids of the eye when open, a superior projection on said body posterior to said ocular prosthesis extending on an axis arranged at approximately 90 degrees to the axis of said posterior projection, said superior projection sized, shaped and positioned to engage and support a levator muscle of the upper eyelid and prevent a superior sulcus deformity behind the upper eyelid.

2. An orbital enucleation implant as recited in claim 1, wherein said posterior projection has a rounded end and said superior projection has a rounded end.

3. An orbital enucleation implant as recited in claim 1, wherein said superior projection defines a cavity in a posterior surface thereof to receive a superior rectus muscle of the eye.

4. An orbital enucleation implant as recited in claim 1, wherein a flange is provided extending between lateral surfaces of said implant around an inferior surface of said implant, said flange being positioned to provide a site for attachment of extraocular muscles of the eye and being shaped to permit a surgical suture needle to pass therethrough.

5. An orbital enucleation implant as recited in claim 4, wherein lateral sides and an inferior side of said implant are flattened extending partially along said posterior projection up to said flange to provide platforms to receive lateral rectus and inferior rectus muscles of the eye, respectively.

6. An orbital enucleation implant as recited in claim 5, wherein a superior surface of said implant is flattened extending partially along the posterior projection up to said superior projection to provide a platform to receive a superior rectus muscle of the eye, said superior projection defining a cavity in a posterior surface thereof adjacent to said flattened surface on said superior surface of said implant to receive the superior rectus muscle.

7. An orbital enucleation implant as recited in claim 4, wherein said anterior surface is three dimensionally curved extending vertically from the top of said superior projection to said flange and laterally from said flange on one lateral side to said flange on the other lateral side.

8. An orbital enucleation implant as recited in claim 1, wherein a superior surface of said body extending partially along said posterior projection and to said superior projection is flattened to provide a platform to receive a superior rectus muscle of the eye.

9. An orbital enucleation implant as recited in claim 1, wherein said biocompatible material is a porous material adapted to receive and promote tissue ingrowth.

10. An orbital enucleation implant as recited in claim 9, wherein said biocompatible material comprises porous polyethylene.

11. An orbital enucleation implant for replacing a volume of an eyeball in an anophthalmic eye socket of an eye, said implant being made of a biocompatible material having an anterior face for coupling to an ocular prosthesis, and having an elongated shape to define a posterior projection having a conical shape to parallel orbital contours of posterior portion of an orbit of the eye socket and having an anterior to posterior dimension configured to project through the optic nerve aperture in Tenon's capsule when said implant is enclosed in Tenon's capsule in the eye socket, a surface of an anterior portion of said implant being shaped to define site, for suturing rectus muscles of the eye to said implant, said conical shape being formed with channels extending up to said sites, said depressions being shaped, sized and positioned to receive and position said rectus muscles.

12. An orbital enucleation implant as recited in claim 11, wherein superior and inferior sides of said implant and lateral sides of said implant are flattened along a portion of said posterior projection and extending up to said sites to define said depressions as platforms for receiving and positioning said rectus muscles.

13. An orbital enucleation implant as recited in claim 12, wherein said surface of said anterior portion includes a flange extending from one lateral side to the other lateral side of said implant around an inferior side of said implant to define the sites for suturing said lateral and inferior rectus muscles to said implant.

14. An orbital implant as recited in claim 11, wherein said anterior face is three dimensionally curved.

15. An orbital implant as recited in claim 11, wherein said biocompatible material is a porous material adapted to receive and promote tissue ingrowth.

16. An orbital implant as recited in claim 15, wherein said biocompatible material comprises porous polyethylene.

17. An orbital enucleation implant for replacing a volume of an eyeball of anophthalmic socket of an eye comprising a rounded body defining an anterior surface shaped, sized and positioned to be coupled to an ocular prosthesis which will extend under and be overlapped by upper and lower eyelids of the eye when open and having a superior projection on said body posterior to said ocular prosthesis shaped, sized and positioned to engage and support a levator muscle of the upper eyelid, fill out a superior sulcus and prevent posterior migration of the pre-aponeurotic fat pad of the upper eyelid, said body being shaped to define a site for suturing a superior rectus muscle of the eye to the body at the base of said superior projection and to define sites for suturing lateral, medial and inferior rectus muscles of the eye to said body adjacent to said anterior face.

18. An orbital enucleation implant as recited in claim 17, wherein a cavity is defined in a posterior side of said superior projection to define said site for suturing said superior rectus muscle to said body.

19. An orbital enucleation implant as recited in claim 17, wherein said body is provided with a flange extending between lateral sides of said body around an inferior side of said body to define the sites for attaching said lateral, medial and inferior rectus muscles to said body.

20. In an orbital enucleation implant as recited in claim 17, wherein said biocompatible material comprises a porous material adapted to receive and promote tissue ingrowth.

21. An orbital enucleation implant as recited in claim 20, wherein said material is porous polyethylene.

* * * * *

UNITED STATES PATENT AND TRADEMARK OFFICE
CERTIFICATE OF CORRECTION

PATENT NO. : 5,466,258
DATED : November 14, 1995
INVENTOR(S) : Peter A. D. Rubin It is certified that error appears in the above-indentified patent and that said Letters Patent is hereby corrected as shown below:

Column 3, line 32, "Tenoh's" should be "Tenon's".

Column 6, claim 11, line 30, "site, for" should be "sites for"; and
line 33, "depressions" should be "channels".

Column 6, claim 12, line 38, "depressions" should be "channels".

Signed and Sealed this

Thirteenth Day of August, 1996

Attest:

BRUCE LEHMAN

*Attesting Officer*     *Commissioner of Patents and Trademarks*